United States Patent
Heckele et al.

[11] Patent Number: 6,059,325
[45] Date of Patent: May 9, 2000

[54] COUPLING FOR CONNECTING A TUBING TO A MEDICAL INSTRUMENT, APPARATUS OR OTHER TUBING

[75] Inventors: Helmut Heckele; Thomas Pöschko, both of Knittlingen, Germany

[73] Assignee: Richard Wolf GmbH, Knittlingen, Germany

[21] Appl. No.: 08/903,875

[22] Filed: Jul. 31, 1997

[30] Foreign Application Priority Data

Sep. 13, 1996 [DE] Germany .................. 196 37 266

[51] Int. Cl.⁷ .................................................. F16L 37/50
[52] U.S. Cl. ...................... 285/325; 285/261; 285/283
[58] Field of Search ............................ 285/325, 326, 285/327, 261, 87, 184, 283, 924

[56] References Cited

U.S. PATENT DOCUMENTS

| | | | |
|---|---|---|---|
| Re. 19,244 | 7/1934 | Robbins | 285/261 |
| 109,332 | 11/1870 | McGowan | 285/261 |
| 1,175,440 | 3/1916 | Hagen | 285/325 |
| 1,317,193 | 9/1919 | Kiel | 285/261 |
| 1,474,155 | 11/1923 | Krause | 285/261 |
| 1,487,517 | 3/1924 | Krause | 285/261 |
| 1,570,180 | 1/1926 | Pulliam | 285/261 |
| 1,994,007 | 3/1935 | Tallant et al. | 285/325 |
| 1,996,218 | 4/1935 | Swanson | 285/325 |
| 2,056,562 | 10/1936 | Bridge | 285/325 |
| 2,190,220 | 2/1940 | Schilling | 285/261 |
| 2,726,881 | 12/1955 | Howard | 285/261 |
| 4,180,285 | 12/1979 | Reneau | 285/261 |

FOREIGN PATENT DOCUMENTS

| | | | |
|---|---|---|---|
| 0 634 190 A2 | 1/1995 | European Pat. Off. | |
| 572584 | 3/1933 | Germany | 285/261 |
| 2 356 093 | 7/1974 | Germany | |
| 33 14 640 A1 | 11/1983 | Germany | |
| 258 746 A5 | 8/1988 | Germany | |
| 493683 | 9/1955 | Italy | 285/261 |
| 682007 | 6/1993 | Switzerland | 285/924 |
| 24013 | 8/1907 | United Kingdom | 285/87 |
| 169717 | 10/1922 | United Kingdom | 285/261 |
| WO 93/08870 | 5/1993 | WIPO | |

*Primary Examiner*—Eric K. Nicholson
*Attorney, Agent, or Firm*—Akin, Gump, Strauss, Hauer & Feld, L.L.P.

[57] ABSTRACT

The coupling consists of two releasably coupleable coupling parts of which one coupling part is allocated an instrument, apparatus or other tubing and the other coupling part is to be connected to another tubing. In the coupled condition one coupling part with a convex spherical surface lies against a concave spherical surface formed on the neighbouring region of the other coupling part. With this, both coupling parts are sealingly axially braced against one another.

2 Claims, 1 Drawing Sheet

COUPLING FOR CONNECTING A TUBING TO A MEDICAL INSTRUMENT, APPARATUS OR OTHER TUBING

BACKGROUND OF THE INVENTION

The invention relates to a coupling for connecting a tubing to a medical instrument, apparatus or other tubing, consisting of two releasable coupleable coupling parts of which the second coupling part is allocated to the instrument, apparatus or other tubing and the other first coupling part is to be connected to the first mentioned tubing, wherein in the coupled condition the first coupling part with a convex spherical surface lies against a concave spherical surface formed on the neighbouring region of the second coupling part, and both coupling parts are sealingly axially braced against one another.

Couplings are known which by way of balls, threads (EP-A-0 634 190) or by way of bayonette connections (Luer couplings), permit the coupling of tubings to medical instruments and apparatus. The disadvantage with such couplings is that the coupling and decoupling of tubings to medical instruments and apparatus is only simple and safe when the coupling parts are well accessible so that they can be easily gripped with the fingers and rotated off. Since all these couplings require a rotation at least of one coupling part about the axis, then particularly when on the coupling part to be rotated there is connected a tubing with a small modulus of elasticity, with a frequent coupling and decoupling, the tubing is excessively stressed.

There are also couplings known (DD 258 746 A5) from which the invention proceeds and with which the longitudinal axes of both coupling parts, before being connectable to one another, must firstly be aligned exactly flush with one another, since the coupling parts can only then be inserted together and connected. Such couplings are quite complicated with regard to their handling. This also applies in the same sense to couplings which are represented and described in DE 33 14 640 A1, DE 23 56 093 A1 and WO 93/08870.

BRIEF SUMMARY OF THE INVENTION

It is therefore the object of the invention, as far as this is concerned, to provide an improved coupling which is easier in its handling. Furthermore the coupling should also permit tubings to be securely and quickly coupled and decoupled under hygienic conditions and above all securely hold together under high pressure. Moreover the coupling must finally be simple and able to be manufactured inexpensively.

Proceeding from a coupling of the previously mentioned type, according to the invention, this object is achieved in that the coupling is designed such that the first coupling part, with its convex spherical surface resting on the concave spherical surface, can be pivoted into a receiver located on the second coupling part and for releasing the coupling can be pivoted out of this receiver.

Both coupling parts may therefore be connected to one another and again released from each other in a relatively uncomplicated manner by way of a simple pivoting procedure, wherein particularly during the connection procedure the mutual resting of the spherical surfaces on one another, in principle automatically provides for a correct alignment of the coupling parts.

In a preferred embodiment form, the convex spherical surface of the first coupling part is formed by a spherical head onto which connects a cylindrical extension towards the free end of the first coupling part. The cylindrical extension at the same time may have a smaller diameter than the spherical head.

The first coupling part comprises, on the cylindrical extension, a projecting shoulder whilst the second coupling part comprises a receiver, for the first coupling part, axially protruding beyond the concave spherical surface and at its free end having at least one bend perpendicular to the longitudinal axis of the coupling, wherein the first coupling part with its spherical head resting against the concave spherical surface is pivotable into the receiver of the second coupling part and wherein the shoulder of the first coupling part rests on the bend of the receiver of the second coupling part. For releasing the coupling the first coupling part may be pivoted out of the receiver in the reverse direction.

The spherical head of the first coupling part and the concave spherical surface of the second coupling part or the coupling parts themselves may be coated with ceramics or may be manufactured from ceramics. It is also possible to use materials of differing elastic ductilities for the coupling parts as a whole, or only for the spherical head and the concave spherical surface. With this it is preferable that the spherical head is manufactured from a material with a higher elastic ductility than that of the material of the spherical surface.

If the spherical head of the first coupling part does not consist of an elastic material which permits, by way of elastic deformation, a sealing against the concave spherical surface of the second coupling part and a clamping pressure against the bend of the extension of the second coupling part, the convex spherical surface may be provided with a seal. With this it is useful when the seal is arranged in an annular groove of the convex spherical surface. It has been shown that an O-ring is useful as a seal of the convex spherical surface.

Finally in order to avoid an undesired lateral pressing out of the first coupling part from the receiver of the second coupling part, the cross section of the receiver should be U-shaped and laterally enclose the first coupling part.

BRIEF DESCRIPTION OF THE DRAWINGS

By way of the drawings, the invention is explained in more detail with an embodiment example. There are shown.

DETAILED DESCRIPTION OF THE INVENTION

Figure 1:
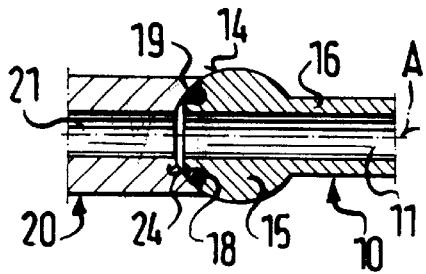
FIG. 1 a cross section of a detail of FIG. 3 at X.

The coupling comprises essentially of a first coupling part 10 and a second coupling part 20. Both coupling parts 10, 20 in the coupled condition comprise axial holes 11, 21 which are flush with one another and lie on the longitudinal axis of the coupling A. The first coupling part comprises a connection piece 12 onto which a tubing 2 may be connected in the known manner.

On its one end the first coupling part 10 has a convex spherical surface 14, whilst the neighbouring end of the second coupling part 20 comprises a concave spherical surface 24 fitting with the convex spherical surface 14 of the first coupling part 10. When the convex spherical surface 14 of the first coupling part 10 is brought to rest against the concave spherical surface 24 of the second coupling part (FIG. 4) and the first coupling part 10 is tilted or pivoted into the position according to FIG. 3, then in a simple manner there is formed a connection of the tubing 2, for example with a suction/rinsing handle 3, wherein simultaneously the spherical surfaces 14, 24 may permit a sealing between the coupling parts in the case that a separate seal is not provided.

Figure 2:
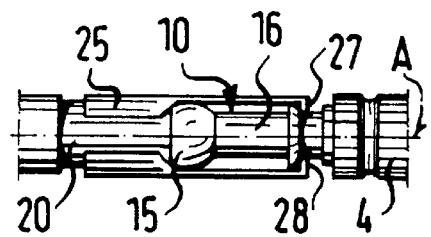
FIG. 2 a plan view of the coupling according to the invention.

The convex spherical surface 14 of the first coupling part is formed by a spherical head 15 onto which there connects a cylindrical extension 16 towards the connection piece 12 of the first coupling part 10. The extension 16 at the same time has a smaller diameter than the spherical head 15. As can be particularly deduced from FIGS. 2 and 4, the first coupling part 10 has a projecting shoulder 17 on the cylindrical extension 16.

The second coupling part 20 comprises a receiver 25 axially jutting beyond its concave spherical surface. This receiver has at its free end two bends 27, 28 perpendicular to the longitudinal axis A of the coupling 1. With this embodiment form, the shoulder 17 of the first coupling part 10, after coupling the first coupling part 10 to the second coupling part 20, internally supports itself against the bends 27, 28 (FIG. 2), by which means a more secure and pressure tight hold of the coupling part 10 in the receiver 25 is made possible.

Figure 3:
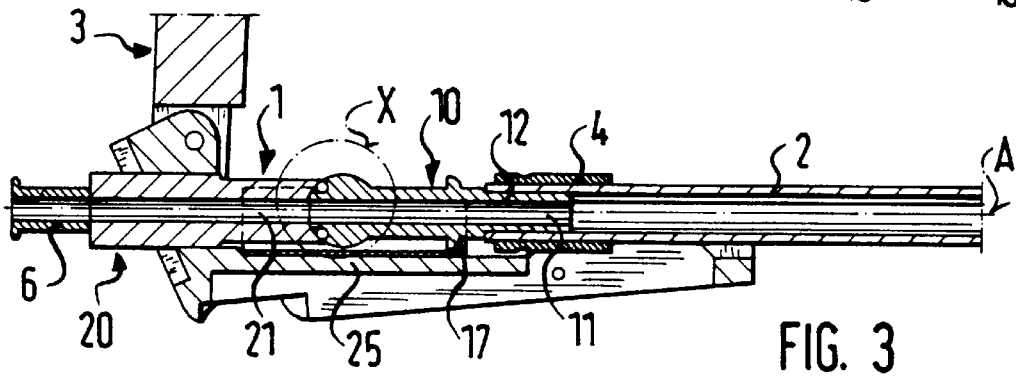
FIG. 3 a longitudinal section through the suction/rinsing handle with the built-on coupling and FIG. 4 a design according to that of FIG. 3, on coupling the coupling.
Figure 4:
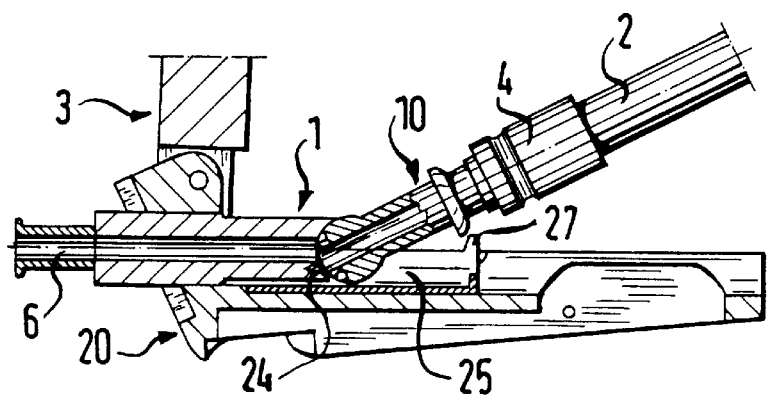

In FIGS. 3 and 4 there is represented an example of the handling of the coupling 1 according to the invention. Here the second coupling part 20 is fastened to the suction/rinsing handle 3 of the known type, whilst the first coupling part is connected to the tubing 2. The tubing 2 is connected to the connection piece of the first coupling part 10 by way of a tubing connecting piece 4. The second coupling part 20 likewise has a connection piece 6 to which, where appropriate, a further tubing may be connected, so that then two tubings may be connected to one another via the coupling.

In FIG. 4 the pivoting in and out of the first coupling part 10 with the tubing 2 connected thereto is shown. If, as with the embodiment example, the spherical head 15 of the first coupling part 10 does not consist of an elastic material then it is necessary for an effective sealing, and to make possible an application force between the shoulder 17 and the bends 27, 28, to admit a seal 18 into the convex spherical surface 14. This seal 18 may consist of an O-ring which is arranged in an annular groove 19 of the convex spherical surface 14 of the first coupling part 10.

After laying the convex spherical surface 14 into the concave spherical surface 14 and after pivoting and pressing the first coupling part 10 into the receiver 25, the first coupling part 10 is securely connected to the second coupling part 29 in an axially unmovable manner by way of the cooperation of the bends 27, 28 and the shoulder 17. In this condition the seal 18 is deformed. For releasing the connection it is only necessary to press and pivot the first coupling part 10 out of the receiver 25 (FIG. 4).

What is claimed is:

1. A coupling for connecting a tubing to a medical instrument, apparatus or other tubing, comprising first and second releasable coupleable coupling parts of which the second coupling part is located on the instrument, apparatus or other tubing and the first coupling part is adapted to be connected to the first mentioned tubing, the first coupling part including a convex spherical surface and the second coupling part including a complementary concave spherical surface, wherein in a coupled condition the first coupling part is positioned with the convex spherical surface lying against the concave spherical surface formed on the second coupling part and both coupling parts are sealingly axially braced against one another, the convex spherical surface of the first coupling part being adapted to be pivoted in the concave spherical surface of the second coupling part such that the first coupling part is engaged into a receiver on the second coupling part in the coupled condition, and for releasing the coupling, the first coupling part is adapted to be pivoted out of the receiver, the convex spherical surface of the first coupling part is formed by a spherical head onto which connects a cylindrical extension, the cylindrical extension has a smaller diameter than the spherical head, wherein the first coupling part, on the cylindrical extension, includes a projecting shoulder and the second coupling part comprises the receiver for the first coupling part, axially protruding beyond the concave spherical surface of said second coupling part and at its free end comprising at least one bend perpendicular to a longitudinal axis of the coupling, such that after pivoting the first coupling part into the receiver of the second coupling part, the shoulder of the first coupling part rests on the bend of the receiver of the second coupling part, the convex spherical surface of the first coupling part being provided with a seal which is arranged in an annular groove of the convex spherical surface, with both of the coupling parts in the coupled condition being axially braced against one another by way of deformation of the seal.

2. A coupling according to claim 1, wherein the seal is an O-ring.

\* \* \* \* \*